United States Patent [19]  [11] 3,966,903
Torii et al. [45] June 29, 1976

[54] SULFITE OR BISULFITE HAIR-WAVING COMPOSITION CONTAINING A WAVE ACCELERATING AGENT

[75] Inventors: Kenji Torii, Tokyo; Tatsuya Ozawa, Chofu; Kimio Ono, Hidaka; Koichi Iwabe; Hiroumi Horikawa, both of Yokohama, all of Japan

[73] Assignee: Shiseido Co., Ltd., Tokyo, Japan

[22] Filed: Apr. 22, 1974

[21] Appl. No.: 462,603

[30] Foreign Application Priority Data
May 4, 1973 Japan.............................. 48-50141

[52] U.S. Cl................................ 424/71; 8/127.51; 132/7; 424/72; 424/361
[51] Int. Cl.².............................................. A61K 7/09
[58] Field of Search ............... 424/71, 72; 8/127.51; 132/7

[56] References Cited
UNITED STATES PATENTS

| | | | |
|---|---|---|---|
| 2,116,521 | 5/1938 | Kritchevsky ........................ | 8/10.1 |
| 2,540,980 | 2/1951 | Den Beste et al. ................ | 424/72 X |
| 2,719,104 | 9/1955 | Westerberg........................ | 8/10 |
| 2,836,543 | 5/1958 | Watson ............................. | 424/71 X |
| 3,025,218 | 3/1962 | Strain et al. ....................... | 424/72 |
| 3,071,515 | 1/1963 | Wehr ................................. | 424/72 |
| 3,075,821 | 1/1963 | Goldemberg et al. .............. | 8/10 |
| 3,215,605 | 11/1965 | Soloway............................. | 8/10.1 |
| 3,567,363 | 3/1971 | Wolfram ........................... | 424/72 X |
| 3,715,429 | 2/1973 | Amon et al. ...................... | 424/71 |

Primary Examiner—V. D. Turner
Assistant Examiner—Vera C. Clarke

[57] ABSTRACT

A hair-waving composition which comprises (A) at least one main waving agent selected from sulfites and bisulfites and (B) at least one wave accelerating agent selected from alkylene carbonates of the general formula:

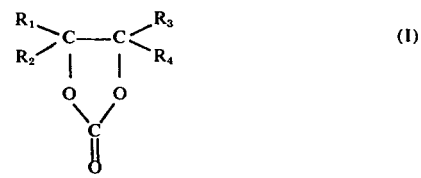

wherein $R_1$, $R_2$, $R_3$ and $R_4$ each stand independently for hydrogen atom, methyl group, ethyl group, hydroxyethyl group or hydroxy methyl group, alkyl carbamates of the general formula:

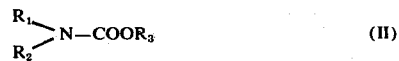

wherein $R_1$, $R_2$ and $R_3$ each stand independently for hydrogen atom, methyl group, ethyl group or propyl group, and γ- or δ-lactones of the general formula:

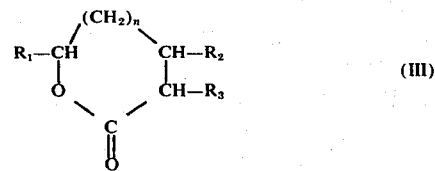

wherein $R_1$, $R_2$ and $R_3$ each stand for hydrogen atom or methyl group, and $n$ for an integer of 0 or 1. This composition can set strong permanent waves with greater safety within the pH range of human skin at a low temperature without any unpleasant odor.

14 Claims, 1 Drawing Figure

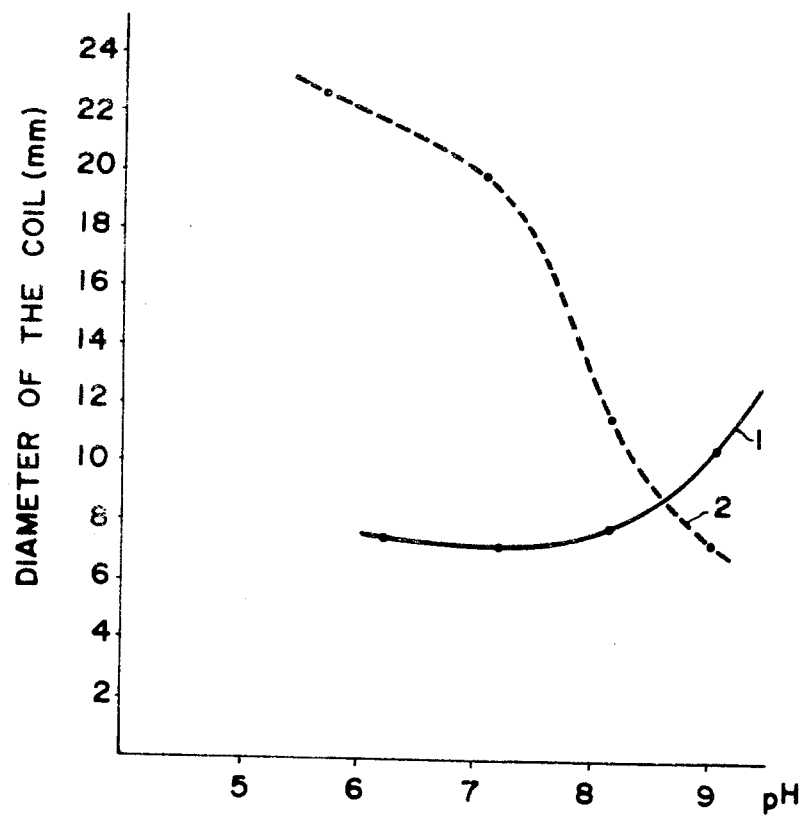

SULFITE OR BISULFITE HAIR-WAVING COMPOSITION CONTAINING A WAVE ACCELERATING AGENT

BACKGROUND OF THE INVENTION

This invention relates to a new composition utilizable for both hair waving and setting. More particularly, this invention relates to a hair-waving composition comprising one or more of specific wave accelerating agents selected from alkylene carbonates, alkyl carbamates and γ- or δ-lactones in addition to the main sulfite or bisulfite waving agent. By the use of this composition, strong permanent waves can be created in hair with greater safety within the pH range of human skin at a low temperature without any unpleasant odor.

The formation of waves in hair is achieved by a combination of the steps of subjecting the hair to a reducing treatment for reductively disrupted cystine linkages (—S—S—) in hair keratin, artificially curling the reductively treated hair by the aid of a rod or the like to form waves and oxidizing the treated hair naturally or by the aid of an oxidizing agent to regenerate cystine linkages in the hair for setting the waves.

Chemicals utilizable in the formation of waves in hair are generally called waving agents and various compounds have been proposed hitherto as such agents. Most widely used at present among such waving agents is the so-called "cold wave solution". According to the conventional method utilized for the cold wave lotion, hair is reductively treated with a waving solution containing as the main waving agent a mercapto compound such as a thioglycolate and then with a neutralizing solution containing a bromate, perborate, or hydrogen peroxide to effect oxidation. This method enables the formation of satisfactory permanent waves at room temperature but still retains many problems to be solved from the standpoint of environmental hygiene and safety in the course of operation. The aforesaid waving solution emits a strong unpleasant odor due to a mercapto compound used therein and bothers operators and customers alike with an unpleasant feeling. This waving solution has to be combined with an alkaline substance such as ammonia as waving accelerating agent. However, addition of an alkaline substance such as ammonia not only brings about an increase in the unpleasant odor but also induces a significant increase in the pH of the solution, thus causing irritation when the solution is brought into contact with the skin.

In the past, hair waving methods wherein a sulfite or bisulfite is used as waving agent were proposed. For example, U.S. Pat. No. 2,400,377 discloses a waving agent which comprises a mixture of an alcohol and water having a bisulfite dissolved therein and British Pat. No. 591,932 discloses a treating agent which comprises a mixture of an alcohol and water having a sulfite dissolved therein. These waving agents were insufficient to produce a satisfactory strong wave in the hair. Accordingly, there is a great demand for a hair-waving product which is satisfactory in hair-waving effect and harmless in handling and hygiene without any unpleasant odor.

BRIEF SUMMARY OF THE INVENTION

It is an object of this invention to provide a hair-waving composition which is free from any unpleasant odor and safer to the human body.

It is another object of this invention to provide a hair-waving composition which exhibits good permanent waving effect at room temperature without using any conjoint heat treatment.

It is still another object of this invention to provide a hair-waving composition which can set good permanent waves in the hair by treating it in a simple one step operation requiring just rinsing the treated hair with sufficient water.

It is further object of this invention to provide a hair-waving product which comprises waving solution and fixing solution and is capable of forming good permanent waves by treating hair in two steps.

Other objects, features and merits of this invention will become apparent from the following description detailed.

DETAILED DESCRIPTION OF THE INVENTION

As a result of much research done to overcome the drawbacks in the prior art and resolve the problems of odor, handling and hygiene of a hair-waving agent containing a sulfite or bisulfite, it has now been found that the hair-waving effect achieved by a sulfite or bisulfite is greatly enhanced by the addition of a certain compound.

In accordance with this invention, there is provided a hair-waving composition which comprises (A) at least one main waving agent selected from sulfites and bisulfites and (B) at least one wave accelerating agent selected from alkylene carbonates of the general formula:

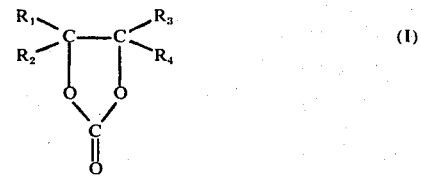

wherein $R_1$, $R_2$, $R_3$ and $R_4$ each stand independently for hydrogen atom, methyl group, ethyl group, hydroxyethyl group or hydroxymethyl group, alkyl carbamates of the general formula:

wherein $R_1$, $R_2$ and $R_3$ each stand independently for hydrogen atom, methyl group, ethyl group or propyl group, and γ- or δ-lactones of the general formula:

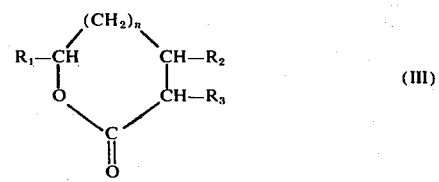

wherein $R_1$, $R_2$ and $R_3$ each stand for hydrogen atom or methyl group, and $n$ for an integer of 0 to 1.

The hair-waving composition of this invention exhibits satisfactory waving effect at a pH value ranging from that of skin to at most weakly alkaline without any conjoint use of alkali and heat. Moreover, this composition is substantially free from any unpleasant odor and is non-irritative to the skin and so gives no particular difficulty in actual use.

In the composition of this invention, at least one compound selected from sulfites and bisulfites (hydrogen sulfites) is used as the main waving agent. Illustrative of these sulfites and bisulfites are lithium, sodium, ammonium, monoethanolamine, diethanolamine, triethanolamine, monoisopropanolamine, diisopropanolamine and triisoproponolamine sulfites and the corresponding hydrogen sulfites. Sulfites and bisulfites utilizable in this invention are not specifically limited to those above exemplified and any sulfite and hydrogen sulfites may freely be used so far as it is soluble and substantially harmless. These salts are substantially odorless and non-irritative to human skin.

Examples of the hair-waving accelerating agents used in this invention and which exhibit an excellent synergistic effect for waving hair when allowed to exist together with the main agent include ethylene carbonate (2-oxo-1,3-dioxoran), propylene carbonate (2-oxo-4-methyl-1,3-dioxoran) and butylene carbonate (2-oxo-4,5-dimethyl-1,3-dioxoran) as the carbonates of the general formula (I); methyl carbamate, ethyl carbamate and ethyl N,N-dimethylcarbamate as the carbamates of the general formula (II); and $\gamma$-butyrolactone, 2-methyl-$\gamma$-butyrolactone, 3-methyl-$\gamma$-butyrolactone, 4-methyl-$\gamma$-butyrolactone ($\gamma$-valerolactone), delta-valerolactone, 5-methyl-$\delta$-valerolactone ($\delta$-caprolactone) and 2,5-dimethyl-$\delta$-valerolactone as the lactones of the general formula (III).

All of these compounds possess no unpleasant odor and high safety in hygiene and are used either alone or in combination of at least two of them. When these compounds are applied together with the main waving agent to hair, they introduce the main agent safely and effectively into the hair cuticle and allow the main ingredient to penetrate into the hair keratin, whereby the waving effect achieved by the main agent is greatly enhanced.

The composition of this invention is prepared by dissolving the main waving agent, the wave accelerating agent and auxiliary additives conventionally used in waving agents of this type homogeneously in a suitable vehicle such as water.

The concentration of the main waving agent in the composition is freely selected in the range of 1–40%, preferably 2–25%, while that of the wave accelerating agent is freely selected in the range of 5–70%, preferably 25–30%, with the proviso that the total of both ingredients should be at least 10% by weight of the total composition but not exceeding 80% by weight, the balance being water and auxiliary additives ordinarily incorporated into the hair waving agents of this type. As the concentrations of the main agent and the accelerating agent become higher, the waving effect tends to be increased. Accordingly, the proportion of these agents can be determined adequately in accordance with the purpose of its intended use. The proportion of the accelerating agent to the main waving agent varies according to the sort of particular promoting agents used and thus cannot be determined definitely. In general, however, the quantity of the accelerating agent is 0.1–20 parts per part of main agent, the all parts being by weight.

The composition of this invention is applied to the hair or to a fibrous material having a chemical structure similar to hair, for example, wool. This composition serves to effect the disruption of cystine linkages in keratin and to facilitate the subsequent after-treatments of the hair. Further, the composition of this invention has a satisfactory waving effect at about the pH of human skin, is safe in handling is free from any unpleasant odor and can be perfumed, if desired.

The composition of this invention can be used in various fields. For example, it can be used in beauty salons as a cold-wave hair solution and as pretreating agent for hair-dyeing, and is effective also as a hair straightener. As the composition is highly in safe, it may be used at home directly by consumers as a curling agent in combination with a set lotion or the like.

Further, the composition is also useful as a curling agent for eye lashes or as a waving agent for wigs and, in different fields, it may be applied as a treating agent for setting and permanent press of keratinous fibers such as wool.

The composition can be utilized independently for simple one-step cold waving as far as a sufficient rinsing with water to remove $HSO_3^-$ or $SO_3^{--}$ can be achieved.

In frequently used conventional permanent waving solutions of a dual liquid system, an aqueous solution containing sodium bromate or hydrogen peroxide is used as a subsequent fixing agent after treatment with the waving solution, but these substances are too strong as oxidizing agent and tend to injure the hair by excessive oxidation.

By using the present invention, the second step of using conventional oxidizing agents such as sodium bromate or hydrogen peroxide can be avoided. A mere but sufficient water rinsing after the treatment is able to remove $HSO_3^-$ or $SO_3^{--}$ and is able to the recover cystine linkages in the hair keratin.

If $HSO_3^-$ or $SO_3^{--}$ is removed chemically by using water soluble salts of barium and calcium, such as barium chloride, barium bromide, barium iodide, barium formate, barium acetate, barium hydroxybenzoate, calcium chloride, calcium bromide, calcium iodide, calcium formate, calcium acetate and calcium hydroybenzoate, the reformation of cystine linkages will be accelerated and be achieved effectively. By this procedure, excessive oxidation which has been a problem in the prior art can be overcome, and strong waves and durable curls in the hair can be obtained.

The composition of this invention may be combined with other additives conventionally used for waving agents, for example, solubilization aids such as ethyl alcohol and propyl alcohol, humectants such as polyethylene glycol and glycerin, thickening agents such as acrylic resins, and other including antioxidants, surfactants and perfumes.

This invention will be understood in more detail by referring to the following examples wherein all parts and percentages are by weight unless otherwise indicated specifically.

EXAMPLE 1

This example shows the results of a test in the waving effect of hair using the treating agent of this invention.
Method of the test:

Ten untreated hairs (10 cm in length) were wound around a glass rod (6.5 mm in diameter), placed in a test solution* (reducing solution) for 10 minutes, and then rinsed for 15 minutes with water. By this treatment, the hairs became curly. The waving effect was evaluated by measuring the curls diameter. Smaller values refer to better effects.

*Test solution

| | | |
|---|---|---|
| Ammonium hydrogen sulfite | 10 % | |
| Wave accelerating substance | 30 % | |
| Deionized (ion-exchanged) water | 60 % | |
| | 100 % | |

Results of the test:
The results are tabulated in Table 1.

Table 1

| Test No. | Wave accelerating substance | Diameter of the curl (mm) |
|---|---|---|
| 1 | ethylene carbonate | 8.5 |
| 2 | ethyl carbamate | 8.5 |
| 3 | γ-butyrolactone | 8.0 |
| 4 | γ-valerolactone | 8.5 |
| 5 | ethanol* | 14.0 |
| 6 | n-propanol* | 12.0 |
| 7 | glycerin* | 16.0 |
| 8 | propylene glycol* | 15.0 |
| 9 | control (No accelerating substance) | 21.0 |

*U.S. Pat. No. 2,400,377

From the test results listed in Table 1, it can be understood that a composition containing as accelerating agent the one contemplated in his invention exhibits remarkable waving effects. The excellent effect of this invention is obvious in comparison with the cases of using alcohols or glycols which have been proposed in the past, not to mention the comparison with the control which contains no accelerating agent.

In the FIGURE of the accompanying drawing there are shown by way of a graph the results of tests on the waving effect at various pH values. In this FIGURE, Curve 1 and Curve 2 designate the results of the tests for a waving agent comprising the composition of this invention (containing hydrogen sulfite together with ethylene carbonate and propylene carbonate) and a conventional waving agent using a mercaptan together with an alkali (commercially available product), respectively. As is evident from this graph, it may be confirmed that the waving agent of this invention exhibits good and sufficient waving effects at a pH range from 6 to 9 in contrast to the limited range of the conventional waving agent using a mercaptan. Therefore, the hair-treating agent of this invention can be used at a pH range near that of the human skin with the merit that the agent is substantially or entirely free from unpleasant odor and safer and less irritating to the skin and causes less damage of the hair.

As to odor, a sensory test on the haair-treating composition of this invention and the conventional waving solution using a mercaptan was conducted using a panel of 100 persons. All of the persons then answered that the hair-treating composition of this invention had no unpleasant odor and was preferable.

As the base itself of the hair-treating composition of this invention is almost odorless, it may properly be perfumed with suitable fragrances.

EXAMPLE 2

This example illustrates the chemical composition of various formulations of the hair-treating composition of this invention.

| Composition A | |
|---|---|
| Ammonium hydrogen sulfite | 20 % |
| Ethylene carbonate | 50 % |
| Propylene glycol | 2 % |
| Antioxidant | proper quantity |
| Perfume | ″ |
| Deionized water | 28 % |
| pH 6.5 | 100 % |

This composition is very efficient in forming and preserving hair waves.

| Composition B | |
|---|---|
| Sodium sulfite | 10 % |
| Sodium hydrogen sulfite | 10 % |
| Ethyl carbamate | 30 % |
| Ethyl alcohol | 10 % |
| Monoethanolamine | 1 % |
| Perfume | proper quantity |
| Antioxidant | ″ |
| Deionized water | 39 % |
| pH 8.5 | 100 % |

This composition has pronounced effect in forming and preserving hair waves.

| Composition C | |
|---|---|
| Monoethanolamine hydrogen sulfite | 3 % |
| Propylene carbonate | 15 % |
| Ethyl carbamate | 10 % |
| Ethyl alcohol | 5 % |
| Glycerin | 5 % |
| Acrylic resin | 2 % |
| Dimethyl alkyl ammonium chloride | 1 % |
| Antioxidant | proper quantity |
| Perfume | ″ |
| Deionized water | 59 % |
| pH 6.5 | 100 % |

This composition is a soft curling composition for home use and can preserve hair setting beautifully.

| Composition D | |
|---|---|
| Potassium hydrogen sulfite | 5 % |
| Urea | 5 % |
| Ethyl carbamate | 20 % |
| Sodium alginate | proper quantity |
| Antioxidant | ″ |
| Perfume | ″ |
| Deionized water | 70 % |
| pH 6.5 | 100 % |

This composition can softly shape hard hair especially of men.

| Composition E | |
|---|---|
| Sodium sulfite | 10 % |
| Ethylene carbonate | 40 % |
| Propylene glycol | 5 % |
| Sodium alginate | 2 % |
| Antioxidant | proper quantity |
| Perfume | ″ |
| Deionized water | 43 % |
| pH 6.5 | 100 % |

This composition can softly shape hair.

| Composition F | |
|---|---|
| Ammonium hydrogen sulfite | 10 % |
| γ-butyrolactone | 30 % |
| Antioxidant | proper quantity |
| Perfume | ″ |
| Deionized water | 60 % | pH 6.5 100 %

This composition is very effective in forming and preserving hair waves.

| Composition G | |
|---|---|
| Monoethanolamine sulfite | 3 % |
| γ-valerolactone | 15 % |
| Ethylene carbonate | 5 % |
| Antioxidant | proper quantity |
| Perfume | " |
| Deionized water | 77 % |
| pH 6.5 | 100 % |

This composition shapes hair softly.

| Composition H | |
|---|---|
| Sodium sulfite | 10 % |
| Ammonium hydrogen sulfite | 15 % |
| δ-valero lactone | 20 % |
| Glycerin | 5 % |
| Antioxidant | proper quantity |
| Perfume | " |
| Deionized water | 50 % |
| pH 6.5 | 100 % |

This composition is highly effective in forming and preserving hair waves.

EXAMPLE 3

A hair waving solution for home use was prepared according to following formulation.

The waving solution was applied on hair in the aforementioned general procedure with rinsing and subsequently the conventional setting lotion was applied to give a permanent hair set.

| waving solution: | |
|---|---|
| Sodium sulfite | 8.0 % |
| Propylene carbonate | 30.0 % |
| Ethanol | 10.0 % |
| Glycerin | 5.0 % |
| Antioxidant | proper quantity |
| Deionized water | 47.0 % |
| | 100.0 % |

This method was found free from unpleasant odor and very effective in forming waves and preserving the set hair beautifully.

EXAMPLE 4

This example shows results of the tests on the waving effect for hair using the waving and fixing solution according to this invention. Method of the test:

Ten untreated hairs (10 cm) were wound around a glass rod (6.5 mm in diameter), immersed in the waving solution* according to this invention for 10 minutes, rinsed with water and then immersed in the fixing solution** of various prescriptions for 15 minutes. By this treatment the hairs became curly. The waving effect was evaluated by measuring the length of the curl. Smaller values refer to better effects.

*waving solution:
| Monoethanolamine hydrogen sulfite | 5.0 % |
|---|---|
| Ethylene carbonate | 30.0 % |

| Deionized water | 65.0 % |
|---|---|
| | 100.0 % |

*Substances used for the known oxidizing agent.

**fixing solution:
Dilute solutions of various compounds at their optimal concentrations were used. Results of the tests:

Table 2

| Test No. | Main compound as the fixing solution | Length of the curl (mm) |
|---|---|---|
| 1 | 10% Barium acetate | 21 |
| 2 | 10% Barium chloride | 22 |
| 3 | 10% Barium bromide | 21 |
| 4 | 10% Barium iodide | 23 |
| 5 | 15% Calcium acetate | 20 |
| 6 | 15% Calcium chloride | 21 |
| 7 | 15% Calcium bromide | 23 |
| 8 | 15% Calcium iodide | 22 |
| 9 | Water | 35 |
| 10 | 3% Sodium bromate | 42 |
| 11 | 3% Hydrogen peroxide | 50 |
| 12 | Untreated control (No rinse) | 87 |

*Substances used for the known oxidizing agent.

As is evident from Table 2, a combination of the waving solution containing a sulfite salt as main ingredient with the aforementioned fixing solution is confirmed to attain such a high waving effect as has never been attained by a combination of the waving solution with an oxidizing agent.

For the purpose of comparison, the results obtained by using a combination of the waving solution with a dilute solution (1–3% aqueous solution) of sodium bromate or hydrogen peroxide and the results obtained by using the waving solution alone (untreated control) are also shown in Table 2.

EXAMPLE 5

This example various illustrates compositional combinations of waving and fixing solutions according to this invention.

| Combination A | |
|---|---|
| waving solution: | |
| Ammonium hydrogen sulfite | 10.0 % |
| Ethylene carbonate | 15.0 % |
| Polyethylene glycol | 2.0 % |
| Antioxidant | proper quantity |
| Deionized water | 73.0 % |
| | 100.0 % |
| fixing solution: | |
| 5 % aqueous solution of barium chloride | |

Such a permanent wave producing agent possesses no unpleasant odor and is safe and remarkable in the effect for forming and preserving hair waves.

COMBINATION B

Waving solution:
Identical to Combination A
Fixing solution:
20% aqueous solution of calcium acetate As with Combination A, strong hair waves were obtained by this combination.

What is claimed is:

1. A hair-waving composition which comprises

A. from 1 to 40% by weight of a main waving agent selected from the group consisting of a water soluble sulfite and a water soluble hydrogen sulfite and B. from 5 to 70% by weight of a wave accelerating agent selected from the group consisting of an alkylene carbonate of the formula:

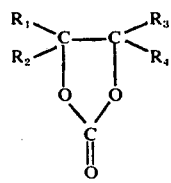

(I)

wherein $R_1$, $R_2$, $R_3$ and $R_4$ each stand independently for hydrogen, methyl or ethyl, an alkyl carbamate of the formula:

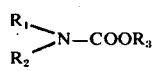

(II)

wherein $R_1$, $R_2$ and $R_3$ each stand independently for hydrogen, methyl, ethyl or propyl and a $\gamma$- or $\alpha$- lactone of the formula:

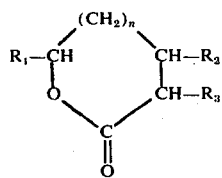

(III)

wherein $R_1$, $R_2$ and $R_3$ each stand for hydrogen or methyl, and $n$ for an integer of 0 or 1, and mixtures thereof, and C. water wherein the total amount of (A) and (B) ranges from 10 to 80% by weight.

2. The composition according to claim 1 wherein said main waving agent is selected from the group consisting of sodium sulfite, potassium sulfite, ammonium sulfite, sodium hydrogen sulfite, potassium hydrogen sulfite, ammonium hydrogen sulfite, monomethanolamine hydrogen sulfite and monopropanolamine hydrogen sulfite.

3. The composition according to claim 1 wherein said wave accelerating agent is selected from the group consisting of ethylene carbonate and propylene carbonate.

4. The composition according to claim 1 wherein said wave accelerating agent is selected from the group consisting of methyl carbamate and ethyl carbamate.

5. The composition according to claim 1 wherein the wave accelerating agent is selected from the group consisting of $\gamma$-butyrolactone, 4-methyl-$\gamma$-butyrolactone and $\delta$-valerolactone.

6. The composition according to claim 1 wherein the amount of the said main waving agent ranges from 2 to 25% by weight.

7. The composition according to claim 1 wherein the amount of said wave accelerating agent ranges from 25 to 30% by weight.

8. The hair-waving composition according to claim 1 additionally including a hair-fixing composition for setting permanent waves comprising a water soluble salt of a metal selected from the class consisting of barium and calcium.

9. The hair waving composition according to claim 8 wherein said waving agent is selected from the group consisting sodium sulfite, potassium sulfite, ammonium sulfite, sodium hydrogen sulfite, potassium hydrogen sulfite, ammonium hydrogen sulfite, monoethanolamine hydrogen sulfite, monopropanolamine hydrogen sulfite and mixtures thereof.

10. The hair waving composition according to claim 8 wherein said wave accelerating agent is selected from the group consisting of ethylene carbonate, propylene carbonate and mixtures thereof.

11. The hair waving composition according to claim 8 wherein said waving composition contains 2 to 25% by weight of said main waving agent.

12. The hair waving composition according to claim 8 wherein said waving composition contains 25 to 30% by weight of said wave accelerating agent.

13. The hair waving composition according to claim 8 wherein said fixing composition contains a water-soluble salt of barium selected from the class consisting of barium chloride, barium bromide, barium iodide, barium formate, barium acetate, barium hydroxybenzoate and mixture thereof.

14. The hair waving composition according to claim 8 wherein said fixing composition contains a water-soluble salt of calcium selected from the class consisting of calcium chloride, calcium bromide, calcium iodide, calcium formate, calcium acetate, calcium hydroxybenzoate and mixture thereof.

* * * * *

UNITED STATES PATENT AND TRADEMARK OFFICE
CERTIFICATE OF CORRECTION

PATENT NO. : 3966903
DATED : June 29, 1976
INVENTOR(S) : Kenji Torii et al

It is certified that error appears in the above-identified patent and that said Letters Patent are hereby corrected as shown below:

Claim 1, column 9, line 26 change "$A$" to --$S$--

Signed and Sealed this

Twelfth Day of October 1976

[SEAL]

Attest:

RUTH C. MASON
*Attesting Officer*

C. MARSHALL DANN
*Commissioner of Patents and Trademarks*